United States Patent [19]

Gedeon et al.

[11] 4,268,498

[45] May 19, 1981

[54] CLEAR COSMETIC STICKS

[75] Inventors: Harvey Gedeon, Monsey; James F. Joyce, Brooklyn; David Kellner, Hollis, all of N.Y.

[73] Assignee: Revlon, Inc., New York, N.Y.

[21] Appl. No.: 57,568

[22] Filed: Jul. 16, 1979

[51] Int. Cl.³ .......................... A61K 7/42; A61K 7/44
[52] U.S. Cl. .................... 424/59; 252/522A; 424/DIG. 5; 424/60; 424/65; 536/119; 536/120
[58] Field of Search ............ 424/59, 60, DIG. 5, 424/65; 536/119, 120

[56] References Cited

U.S. PATENT DOCUMENTS

| Re. 23,443 | 12/1951 | Lolkema | 536/120 |
|---|---|---|---|
| 1,320,855 | 11/1919 | Henderson | 424/DIG. 5 |
| 2,459,108 | 11/1943 | Lolkema | 536/120 |
| 2,617,754 | 11/1952 | Neely | 424/DIG. 5 |
| 2,626,935 | 6/1953 | De Groote | 536/119 |
| 2,927,919 | 3/1960 | Anderson | 536/120 X |
| 2,945,024 | 7/1960 | De Groote et al. | 536/120 |
| 2,945,025 | 7/1960 | De Groote et al. | 536/120 |
| 2,974,134 | 3/1961 | Pollitzer | 536/120 |
| 3,148,125 | 9/1964 | Strianse et al. | 424/DIG. 5 |
| 3,154,470 | 10/1964 | Braun et al. | 424/DIG. 5 |
| 3,190,927 | 6/1965 | Patton, Jr. et al. | 536/120 |
| 3,480,616 | 11/1969 | Osipow et al. | 536/119 |
| 3,856,931 | 12/1974 | Fuchs et al. | 424/14 |
| 4,151,304 | 4/1979 | Evans | 536/119 |

FOREIGN PATENT DOCUMENTS

| 37-4448 | 6/1962 | Japan | 424/36 |
|---|---|---|---|
| 51-14488 | 5/1976 | Japan | 536/119 |

Primary Examiner—Dale R. Ore
Attorney, Agent, or Firm—Leon E. Tenenbaum

[57] ABSTRACT

A composition for use as a base in clear cosmetic sticks comprises water, lower alkyl ester of fatty acid, propylene glycol, sodium salt of fatty acid, polyoxypropylene ether of a long chain alcohol, polyoxyethylene ether of a long chain alcohol, and polyoxyethylene-glucose-fatty acid ester.

6 Claims, No Drawings

CLEAR COSMETIC STICKS

This invention relates to cosmetics. It particularly relates to substantially clear sticks, in which there are incorporated high levels of cosmetically active ingredients.

The use of clear sticks to apply cosmetically active ingredients to the skin is well known in the cosmetic art. Such sticks are comprised of sodium stearate as the primary gellant, alcohol and the desired cosmetically active ingredient as essential ingredients. However, such sticks have a hazy or cloudy appearance and, even if they are clear when made, will tend to opacify with time, which does not add to their attractiveness. Furthermore, due to the slow evaporation of the alcohol, there is a considerable shrinkage of the stick, which may at times result in the stick falling out of its holder when in use.

The use of solvents having a much slower rate of evaporation than alcohol, such, as for example, glycerine, propylene glycol or ethylene glycol, does reduce the rate of evaporation. However, such sticks are still hazy and have the further disadvantage of being irritating to the skin. The sticks also exhibit considerable syneresis and/or cloudiness with time.

The use of alkoxylated alcohols to provide clear emollient sticks has been recommended by a supplier of such alcohols. However, when high levels of cosmetically active ingredients were added to such compositions they also turned hazy.

It is, accordingly, an object of the present invention to provide an aesthetically acceptable, substantially clear stick which can accommodate high levels of cosmetically acceptable ingredients such as fragrances and sunscreens.

It is another object of the present invention to provide a substantially clear fragrance stick which does not shrink on standing.

It is a further object of the present invention to provide a substantially clear cosmetic stick which is non-irrating to the skin.

Other objects will appear from the description which follows.

In accordance with the present invention there is provided a substantially clear cosmetic stick which contains as essential ingredients in parts by weight:

| | |
|---|---|
| polyoxyethylene (17–23)-glucose-fatty acid ester | 2–5 |
| polyoxyethylene (20–26) ether of a long chain alcohol | 2–5 |
| polyoxypropylene (2–5) ether of a long chain alcohol | 24–72 |
| sodium salt of a fatty acid | 5–8 |
| propylene glycol | 5–10 |
| lower alkyl ester of fatty acids | 5–10 |
| water | 2–5 |
| cosmetically active ingredient | 3–40 |

The numbers in parenthesis refer to the number of monomer units in the polymer.

The glucose unit in the polyoxyethylene (17–23) glucose fatty acid ester is preferably methylated.

The long chain alcohols contain from 10 to 20 carbon atoms and include such alcohols as lauryl, myristyl, palmityl and the like. The fatty acid moiety in the salts or esters contains from 12 to 20 carbon atoms and includes such acids as dodecanoic, myristic, palmitic, oleic, stearic and the like. The lower alkyl moiety in the esters contains from 1 to 6 carbon atoms and may be branched or straight-chained. Suitable alkyl groups are methyl, ethyl, propyl, isopropyl, butyl, isobutyl, isoamyl and the like.

Preferably, the polyoxyethylene-glucose-fatty acid esters contain about 20 monomer units, the polyoxyethylene ethers of long chain alcohols contain about 23 monomer units, and the polyoxypropylene ethers of long chain alcohols contain about 3 monomer units.

The preferred polyoxyethylene-glucose-fatty acid ester is poloxyethylene (20) methyl-glucoside sesquistearate.

Any acceptable cosmetically active ingredient which dissolves to yield a clear composition is suitable for use in the compositions of the present invention. These ingredients include fragrances, such as green floral and chypre, sunscreens, skin conditioners, nail conditioners, deodorants and the like.

If desired, preservatives and colorants may be added. Suitable preservatives include the methyl and propyl parabens and benzethonium chloride.

In preparing the substantially clear cosmetic sticks of the present invention all of the ingredients, except the cosmetically active ingredient, were mixed and heated with agitation at about 92° to 98° C. under total reflux until a clear solution was obtained. The solution was cooled to about 70° C. and the cosmetically active ingredient added with stirring and stirring continued until complete solution occurred. The solution was then cooled to about 67° C. and poured into suitable molds.

The following examples illustrate representative substantially clear cosmetic sticks of the present invention. These examples are given by way of illustration and are not to be considered as limiting. The amounts in the examples refer to weight percent.

EXAMPLE 1

| MAXIMUM PROTECTION DEODORANT STICK | |
|---|---|
| PPG MYRISTYL ETHER | 71.55 |
| PROPYLENE GLYCOL | 10.00 |
| WATER | 3.50 |
| SODIUM STEARATE | 5.00 |
| METHYL GLUCETH-20 SESQUISTEARATE | 2.00 |
| LAURETH-23 | 4.00 |
| METHYL PARABEN | 0.30 |
| PROPYL PARABEN | 0.15 |
| BENZETHONIUM CHLORIDE | 0.50 |
| FRAGRANCE | 3.00 |

EXAMPLE 2

| SOLID PERFUME STICK | |
|---|---|
| PPG MYRISTYL ETHER | 42.55 |
| PROPYLENE GLYCOL | 10.00 |
| ISOPROPYL MYRISTATE | 10.00 |
| WATER | 3.50 |
| SODIUM STEARATE | 5.00 |
| METHYL GLUCETH-20 SESQUISTEARATE | 2.00 |
| LAURETH-23 | 4.00 |
| METHYL PARABEN | 0.30 |
| PROPYL PARABEN | 0.15 |
| BENZETHONIUM CHLORIDE | 0.50 |
| FRAGRANCE | 20.00 |

EXAMPLE 3

| SOLID PERFUME STICK | |
| --- | --- |
| PPG MYRISTYL ETHER | 24.55 |
| PROPYLENE GLYCOL | 10.00 |
| ISOPROPYL MYRISTATE | 10.00 |
| WATER | 3.50 |
| SODIUM STEARATE | 5.00 |
| METHYL GLUCETH-20 SESQUISTEARATE | 2.00 |
| LAURETH-23 | 4.00 |
| METHYL PARABEN | 0.30 |
| PROPYL PARABEN | 0.15 |
| BENZETHONIUM CHLORIDE | 0.50 |
| FRAGRANCE | 40.00 |

EXAMPLE 4

| FRAGRANCE STICK | |
| --- | --- |
| PPG MYRISTYL ETHER | 50.05 |
| PROPYLENE GLYCOL | 10.00 |
| ISOPROPYL MYRISTATE | 9.50 |
| WATER | 3.50 |
| SODIUM STEARATE | 8.00 |
| METHYL GLUCETH-20 SESQUISTEARATE | 2.50 |
| LAURETH-23 | 3.50 |
| METHYL PARABEN | 0.30 |
| PROPYL PARABEN | 0.15 |
| BENZETHONIUM CHLORIDE | 0.50 |
| FRAGRANCE | 12.00 |

EXAMPLE 5

| SUN BLOCK STICK | |
| --- | --- |
| PPG MYRISTYL ETHER | 42.55 |
| ISOPROPYL MYRISTATE | 10.00 |
| PROPYLENE GLYCOL | 10.00 |
| WATER | 3.50 |
| SODIUM STEARATE | 7.00 |
| METHYL GLUCETH-20 SESQUISTEARATE | 2.00 |
| LAURETH-23 | 4.00 |
| PROPOXYLATED ETHYL PARA-AMINOBENZOATE | 6.00 |
| BENZOPHENONE-3 | 3.00 |
| METHYL PARABEN | 0.30 |
| PROPYL PARABEN | 0.15 |
| BENZETHONIUM CHLORIDE | 0.50 |
| FRAGRANCE | 11.00 |

EXAMPLE 6

| DEODORANT STICK | |
| --- | --- |
| PPG MYRISTYL ETHER | 71.25 |
| PROPYLENE GLYCOL | 10.00 |
| WATER | 3.50 |
| SODIUM STEARATE | 5.00 |
| METHYL GLUCETH-20 SESQUISTEARATE | 2.00 |
| LAURETH-23 | 4.00 |
| TRICLOSAN | 0.30 |
| METHYL PARABEN | 0.30 |
| PROPYL PARABEN | 0.15 |
| BENZETHONIUM CHLORIDE | 0.50 |
| FRAGRANCE | 3.00 |

We claim:

1. A substantially clear cosmetic stick consisting essentially of as essential ingredients in parts by weight:

| | |
| --- | --- |
| polyoxyethylene (17-23)-glucose-fatty acid ester | 2-5 |
| polyoxyethylene (20-60) ether of a long chain alcohol | 2-5 |
| polyoxypropylene (2-5) ether of a long chain alcohol | 24-72 |
| sodium salt of a fatty acid | 5-8 |
| propylene glycol | 5-10 |
| lower alkyl ester of a fatty acid | 5-10 |
| water | 2-5 |
| cosmetically active ingredient | 3-40 | wherein the fatty acid moiety in the salts or esters contains from 12 to 20 carbon atoms, the long chain alcohol moieties contain from 10 to 20 carbon atoms, the lower alkyl moieties contain from 1 to 6 carbon atoms, and the cosmetically active ingredient is selected from the group consisting of fragrances, sunscreens, and deodorants.

2. A cosmetic stick according to claim 1 wherein
the polyoxyethylene (17-23)-glucose-fatty acid ester is a polyoxyethylene (20)-glucose-fatty acid ester,
the polyoxyethylene (20-26) ether of a long chain alcohol is a polyoxyethylene (23) ether of a long chain alcohol, and
the polyoxypropylene (2-5) ether of a long chain alcohol is a polyoxypropylene (3) ether of a long chain alcohol.

3. A composition according to claim 2 wherein the cosmetically active ingredient is a fragrance or a sunscreen.

4. A composition according to claim 3 wherein the polyoxyethylene (20)-glucose fatty acid ester is polyoxyethylene (20)-methyl-glucoside sesquistearate, the polyoxyethylene (23) ether of a long chain alcohol is polyoxyethylene (23) ether of lauryl alcohol, and the polyoxypropylene (3) ether of a long chain alcohol is polyoxypropylene (3) ether of myristyl alcohol.

5. A composition according to claim 4 wherein the sodium fatty acid salt is sodium stearate.

6. A composition according to claim 5 wherein the lower alkyl fatty acid ester is isopropyl myristate.

* * * * *